US00PP15378P3

(12) United States Plant Patent
Boyle

(10) Patent No.: US PP15,378 P3
(45) Date of Patent: Nov. 30, 2004

(54) CACTACEAE PLANT NAMED 'RIO'

(50) Latin Name: *Hatiora×graeseri*
Varietal Denomination: Rio

(75) Inventor: Thomas H. Boyle, Amherst, MA (US)

(73) Assignee: University of Massachusetts, Amherst, MA (US)

( * ) Notice: Subject to any disclaimer, the term of this patent is extended or adjusted under 35 U.S.C. 154(b) by 0 days.

(21) Appl. No.: 10/335,038

(22) Filed: Dec. 31, 2002

(65) Prior Publication Data

US 2004/0128728 P1 Jul. 1, 2004

(51) Int. Cl.[7] ..... A01H 5/00
(52) U.S. Cl. ..... Plt./372
(58) Field of Search ..... Plt./372

(56) References Cited

U.S. PATENT DOCUMENTS

PP11,327 P 4/2000 Boyle, III
6,156,959 A 12/2000 Boyle, III

OTHER PUBLICATIONS

Renate Karle and Thomas H. Boyle, "Relationships between Floral Morphology, Breeding Behavior, and Flower Longevity in Easter Cactus," University of Massachussetts (Amherst, Massachussetts), pp. 296–300, (Feb. 8, 1999).
Renate Karle, Constance A. Parks, Maureen C. O'Leary and Thomas H. Boyle, "Polyploidy–included Changes in the Breading Behavior of *Hatiora×graeseri* (Cacteceae)," University of Massuchussetts (Amherst, Massachussetts), pp. 397–403, (Feb. 8, 2002).
C. Parks and T.H. Boyle, "Variation in Ploidy Level, Fertility, and Breeding Behavior in Cultivated Schlumbergera (Cactaceae)," University of Massachusetts, supported by Can. Int. Dev. Agency (CIDA) (Amherst, Massachussetts), p. 341–346, (2003).

*Primary Examiner*—Anne Marie Grunberg
*Assistant Examiner*—June Hwu
(74) *Attorney, Agent, or Firm*—James R. Cypher; Charles R. Cypher

(57) ABSTRACT

A variety of the Cactaceae family produced by a controlled cross named 'Rio'. 'Rio' has a strong growth habit, a "red" colored bloom, a strong propensity to branch with minimal pruning, erect stems, and blooming flowers that last for two weeks on the plant.

5 Drawing Sheets

Latin name of genus and species of the plant claimed: The new plant is a species of *Hatiora×graeseri* Barthlott ex D. Hunt.

Variety Denomination: The new plant's varietal denomination is 'Rio'.

BACKGROUND OF THE INVENTION

The present invention relates to a new and distinct variety of the Cactaceae family. The new variety is a *Hatiora hybrid* named 'Rio' by the inventor. The inventor is Dr. Thomas Boyle of the University of Massachusetts, residing in Amherst, Mass., a citizen of the United States.

Many members of the Cactaceae family can be forced to bloom in the Northern Hemisphere in the winter. Because they can bloom in the winter there is a large market for these varieties.

This new variety was produced by the inventor by a controlled cross. The new variety is a triploid form derived in part from the diploid *Hatiora* commercial cultivar 'Evita'. 'Evita' was developed by J. de Vries Potplantencultures bv, Aalsmeer, the Netherlands and released in 1983.

The inventor developed the triploid seedling from crossing a tetraploid *Hatiora gaertneri* clone (female parent) with the diploid *Hatiora* cultivar 'Evita' (male/pollen parent). Neither parent is patented in the United States. The ploidy level of 'Rio' (triploid) was determined at the University of Massachusetts from chromosome counts of immature flower buds and root tips.

The overall red appearance of the flower is due to the generally even-toned color of its tepals.

The distinguishing characteristics of the new variety are retained by asexually reproduced, successive generations.

The new variety possesses the desirable characteristics of:

1. a strong growth habit with erect stems;
2. a "red" colored bloom;
3. relatively large flowers;
4. a strong propensity to branch with minimal pruning; and
5. a strong resistance to fungal diseases.

Blooming flowers on the plant can last as long as two weeks at temperatures between 60 and 70 degrees Fahrenheit. Cold temperatures slow down the rate at which buds mature into flowers. Strong light is also necessary for bud development.

The new variety has asexually reproduced by the inventor and under the direction of the inventor at a commercial nursery in Half Moon Bay, Calif. The new variety has been asexually reproduced through three successive generations by cuttings, and it has been found that the combination of characteristics as herein disclosed remain firmly fixed.

The present invention differs from its parents with respect to the following characteristics in Table 1:

| Trait | *H. gaertneri* tetraploid | *H. x graeseri* 'Evita | *H. x graeseri* 'Rio' |
|---|---|---|---|
| Length of mature phylloclades | Between 55 and 80 mm | Between 40 and 60 mm | Between 50 and 65 mm |
| Width of mature phylloclades | Between 28 and 33 mm and averaging about 30 mm | Between 20 and 26 mm and averaging about 23 mm | Between and 28 mm and averaging about 25 mm |
| Color of immature phylloclades | Between RHS 175A and 178A | RHS 137A | Between RHS 175A and 178A |
| Color of perianth segments at maturity | RHS 44 A/B at apices and RHS 26C at base | RHS 74B/C at apices and RHS 74D at base | Overall RHS 45A, RHS 46B in the upper portion and RHS 47D at base |
| Color of filaments at maturity | RHS 158C at base and 48D near apex | RHS 74 B/C | RHS 74 B/C |
| Color of ovaries at maturity | Between RHS 175A and 178A | RHS 137B/C at base and RHS 71A along edges of ribs at distal end | RHS 175A and 178A |
| Color of style at maturity | RHS 155D at proximal end and RHS 33B at distal end | RHS 155D at proximal end and RHS 67B at distal end | RHS 155D at proximal end and red RHS 44A at distal end |
| Pollen diameter (mean ± standard deviation) | 84.0 ± 6.6 microns | 68.2 ± 3.4 microns | 71.3 ± 4.5 microns |
| Stomatal density (number/mm$^2$) | 27.6 ± 8.5 | 14.2 ± 5.0 | 13.8 ± 4.0 |
| Chromosome number | 2n = 4x = 44 | 2n = 2x = 22 | 2n = 3x = 33 |
| Flower diameter | About 60 mm | About 55 mm | 50 to 57 mm |
| Branching | About 1–2 new phylloclades per segment | About 3–4 new phylloclades per segment | About 3 new phylloclades per segment |

BRIEF DESCRIPTION OF THE DRAWING

The accompanying drawings serve, by color photographic means, to illustrate the new plant variety. The colors are represented as truly as possible using conventional photographic procedures.

DETAILED DESCRIPTION OF THE NEW VARIETY

Figure 1:
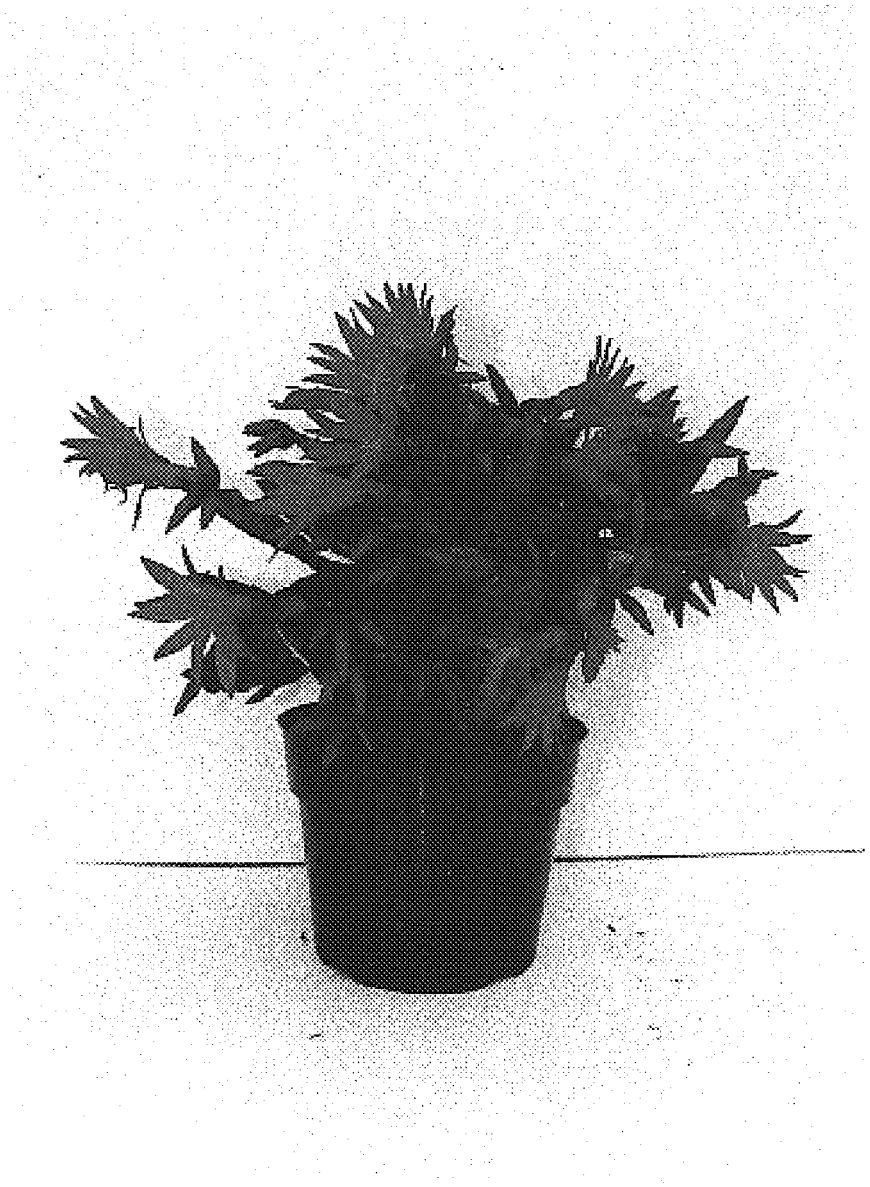
FIG. 1 is a color photograph of several individuals of the new variety illustrating the overall appearance and form of the plants, and the abundance of blooms, when grown in a single pot for commercial sale.
Figure 2:
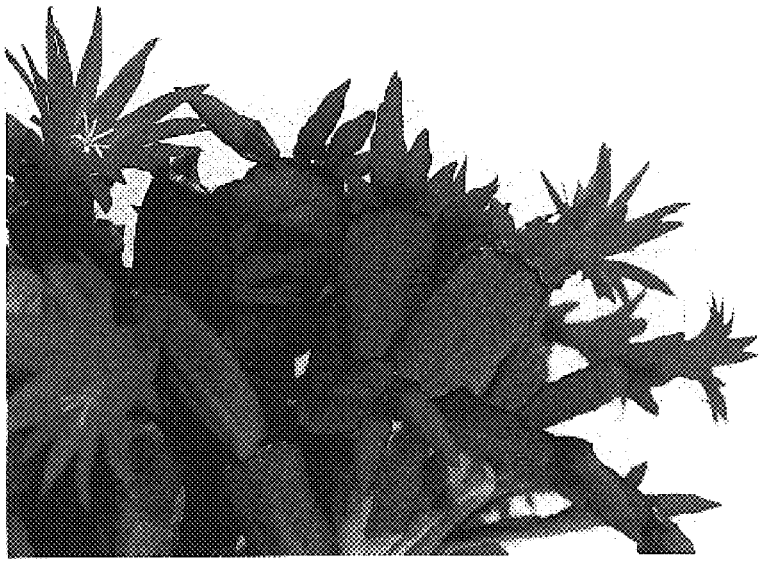
FIG. 2 is a color photograph of several individual flowers of the new variety illustrating the appearance of the bloom in various stages.
Figure 3:
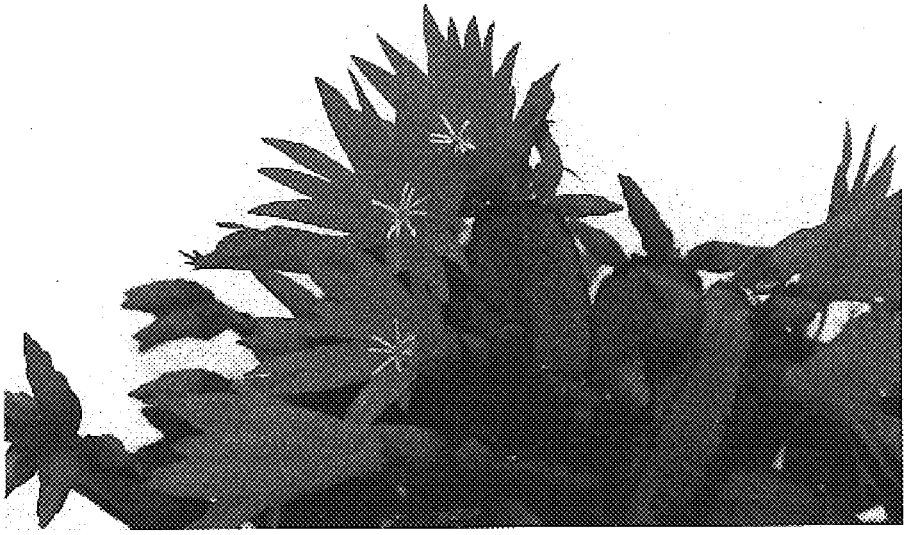
FIG. 3 is a color photograph of one individual plant grown for commercial sale removed from its soil.
Figure 4:
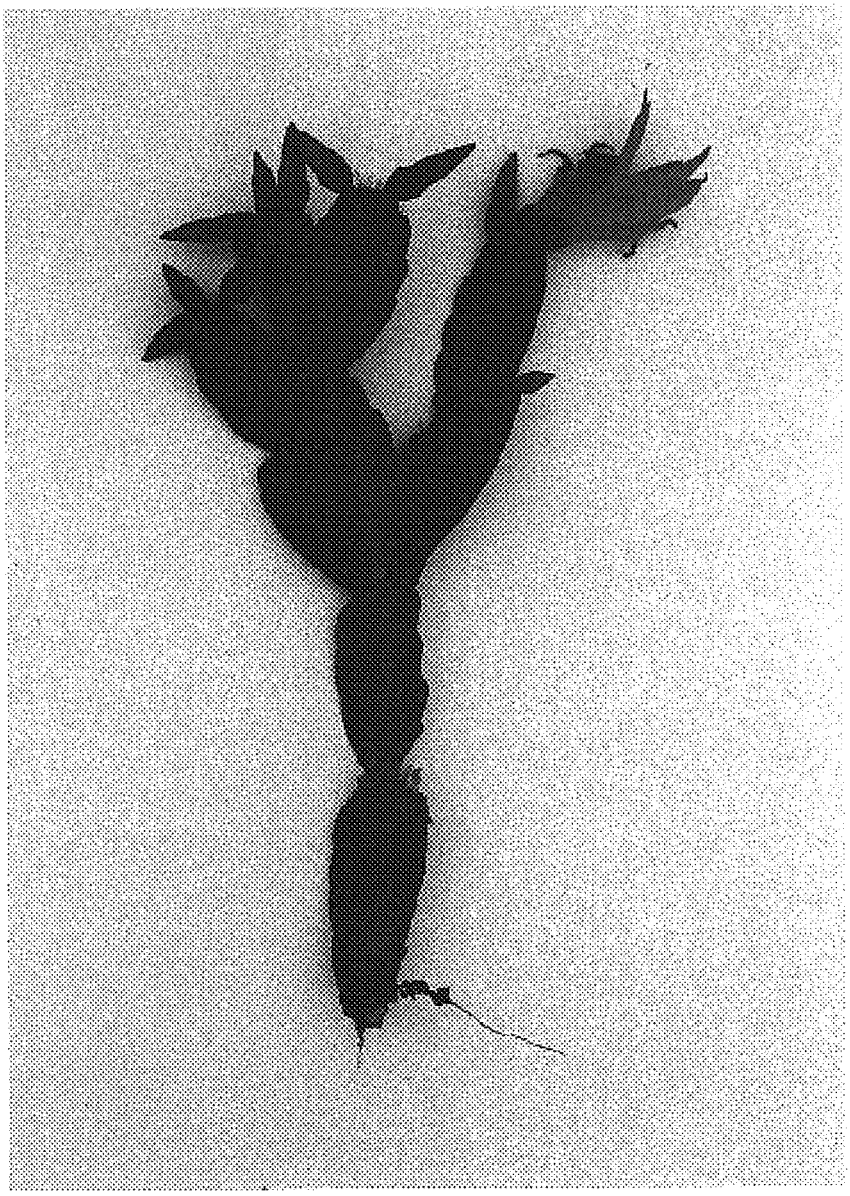
FIG. 4 is a color photograph of an individual plant with all but one of the phylloclades removed from the cutting that was originally planted to show the branching of upper phylloclades on an individual grown for commercial sale.
Figure 5:
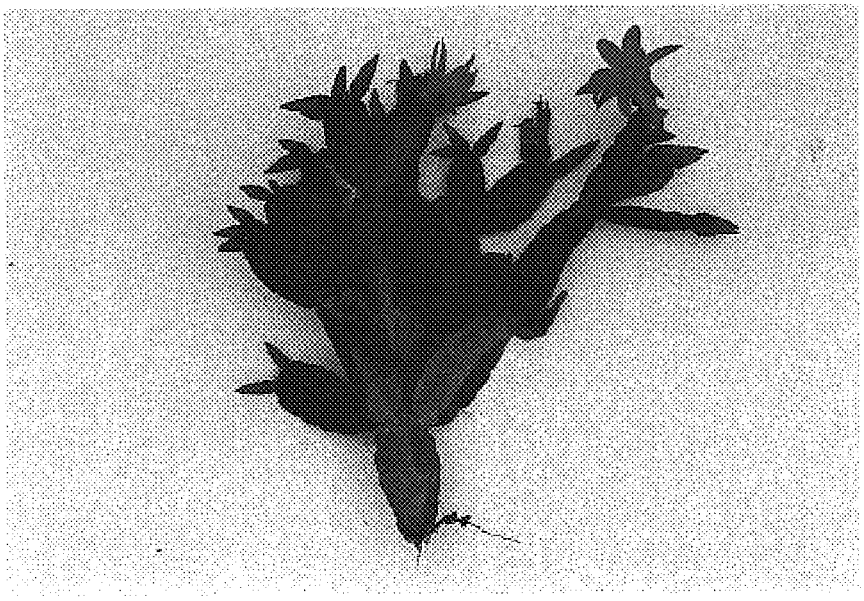
FIG. 5 is a color photograph of an individual plant produced from a single cutting. The plant is shown removed from the soil.
Figure 6:
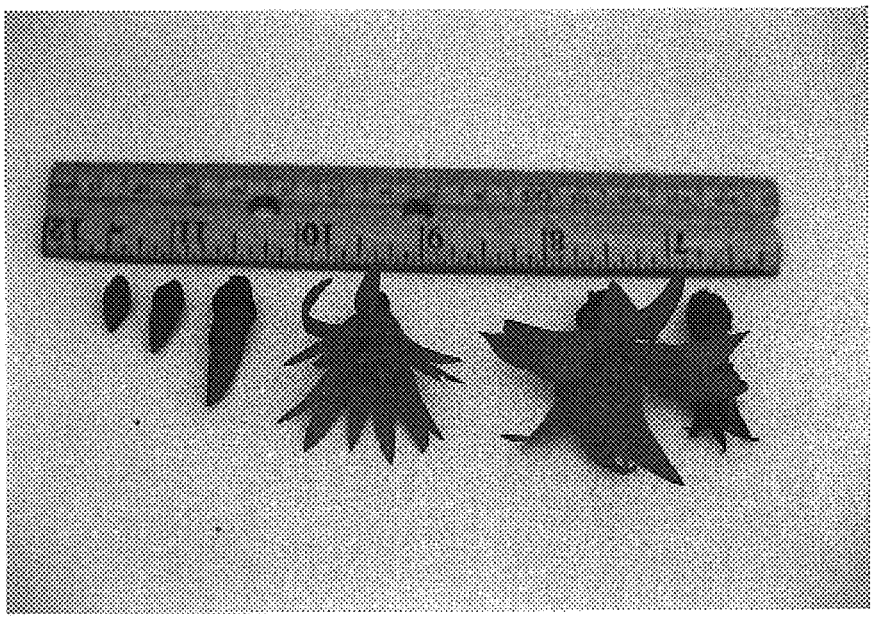
FIG. 6 is a color photograph of flowers of the plant, showing the progression of the flower as it matures.
Figure 7:
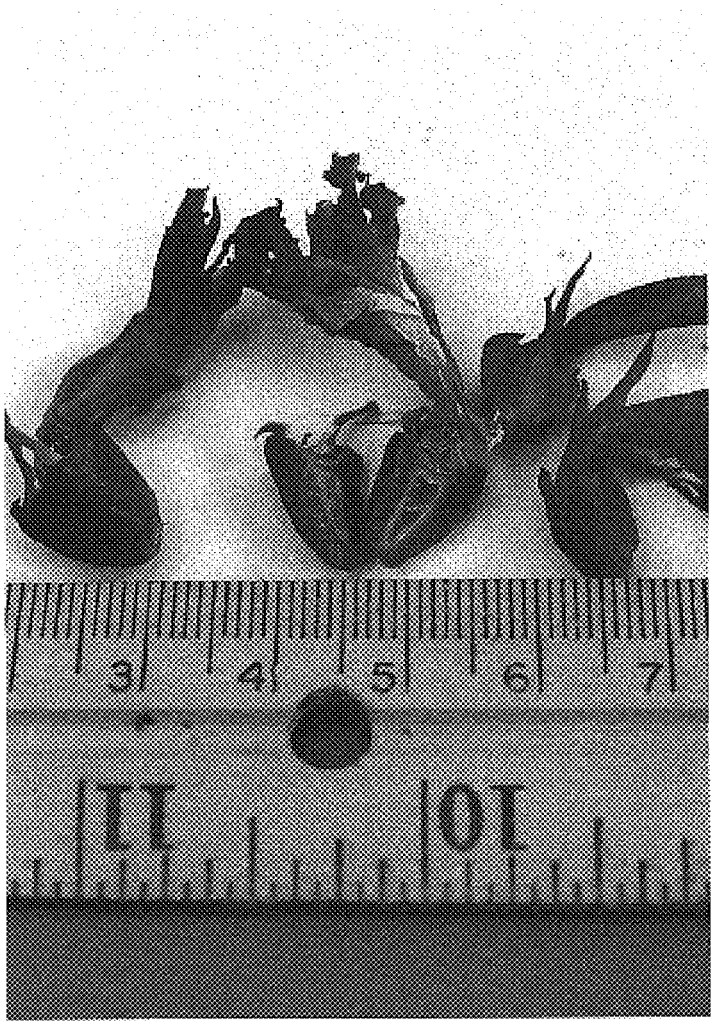
FIG. 7 is a color photograph of multiple ovaries of the plant, the center ovary having been sectioned.

The following is a detailed description of the new variety. The new variety has not been observed under all possible environmental conditions. Color designation and other values may deviate slightly from the stated values from flowering to flowering, but the deviations will be within the range expected from varying environmental, seasonal and cultural conditions. Color designations were made according to The R.H.S. Colour Chart published by The Royal Horticultural Society of London, England.

The plants observed were grown in 6" pots. The plants were approximately 14 months old.

The tallest plants were approximately 9" high, other plants were 8" to 7.5" high, the plants observed had been pruned back once as described below. There were typically 6 or 7 cuttings placed in each pot. Some cuttings had five levels of phylloclades, including the basal phylloclade that was inserted in the dirt, with buds at the top of the highest phylloclades. Most other plants had 4 levels of phylloclades with buds growing on the highest phylloclades.

The following description is based on observations of optimally fertilized plants. The plants were also treated with fungicides and pesticides.

The plants were started in green houses at a commercial nursery in Half Moon Bay, Calif. Temperatures in Half Moon Bay on average range from 55 to 65 degrees Fahrenheit in the summer months, and from 45 to 55 degrees Fahrenheit in the winter months.

The plants started as cuttings taken as entire phylloclades. Cuttings were dried in flats for four weeks to harden. 6 to 7 cuttings were then placed in the same pot. The cuttings were kept under glass while they were rooting. At night, the plants were kept at an average temperature of approximately 64 degrees Fahrenheit, and during the day, the plants were allowed to get as hot as 75 to 80 degrees Fahrenheit. Cuttings generally take a month to begin producing roots and then another month to fully root.

When the plants were between five and eight months old, when the new variety had produced three new levels of phylloclades, the top phylloclades were topped or broken from the stems by twisting.

Then, when plants were at an appropriate height for commercial sale, the plants were moved outside to be exposed to colder temperatures for at least two months. Under the conditions in Half Moon Bay, the exposure to colder temperatures initiates bud formation without having to keep them under glass where day length can be shortened.

DETAILED PLANT DESCRIPTION

Name: 'Rio'.

Parentage:

*Female parent.*—*Hatiora gaertneri* clone.

*Male/pollen parent.*—*Hatiora* commercial cultivar 'Evita'. 'Evita' was developed by J. de Vries Potplantencultures bv, Aalsmeer, the Netherlands and released in 1983.

Classification:

*Family.*—Cactaceae.

*Species.*—*Hatiora×graeseri* Barthlott ex D. Hunt.

Form: Terrestrial, shade-loving, succulent, leafless plant with jointed and branched stems.

Stems:

*General.*—Irregular stems of multi-branching upright, adventitiously rootable, flattened phylloclades that have a prominent midrib. Plants observe had stems that generally consisted of 4 levels of phylloclades, with as many as 6 phylloclades (more commonly 3 to 5 ) growing from apex of phylloclades at first and second levels, with less at upper levels. The flattened phylloclades have a prominent midrib (especially in phylloclades at the base of mature plants) and weakly toothed lateral wings. Plants observed were 8 to 9" high.

*Phylloclades.*—General: Mature phylloclades are generally oblong, elongated, and flattened with wings, and have a transversely elongated, areole bearing, truncated apex. From the transversely elongated apex, the wing margins generally run straight or taper slightly to the basal portions (or occasionally they flare outwardly somewhat), where they then taper and merge through a pointed, basal juncture with the phylloclade therebelow. The margins of the wings are also weakly toothed or weakly crenate and an axillary areole is associated with each blunt tooth. Immature phylloclades are often not flattened, but four-angled, having multiple ribs terminating at axillary areoles. The apex of the phylloclade is transversely elongated, and areole bearing with compound areoles. The lateral margins typically have 4 to 5 alternately spaced axillary areoles. Midrib: Prominent midrib extends longitudinally of phylloclade and continuously through joints. Texture: Phylloclades have a smooth, waxy epidermis. Wax in basal phylloclades and phylloclades inserted in the ground becoming thick, corky and translucent with age. First phylloclade above basal phylloclade will often have thick corky wax at its base and along up its midrib part way. Size: Phylloclades are usually between 40 mm and 65 mm long, with some as short as 20 mm. Mature phylloclades are usually 50 to 65 mm long. Phylloclades bearing flower can be as short as 32 mm long. Phylloclades are generally 2 mm thick at the midrib, and tapering to 1 mm thick at the margins. Phylloclades are generally 13 to 28 mm at their widest point, mature phylloclades average about 25 mm. Color: Mature phylloclades are R.H.S. 137A while young phylloclades are a brighter green: R.H.S. 137C, and immature phylloclades are between R.H.S. 175A (greyed-orange group) and R.H.S. 178A (greyed-red group). Some phylloclades can have dark margins, with the midrib and base of the phylloclade being lighter. Areoles: Terminal areole — Large, compound, elongated, oval-shaped with several acicular bristles, copious multi-cellular hairs, and several buds that may mature into either new phylloclades or flowers. The opposite ends of the areole are located adjacent to subsidiary areoles which are in turn located at the axils of the uppermost blunt teeth located at the distal end of the of phylloclade. The acicular bristles are mostly upright (some bent) bristles in clumps which can be as long as 7 mm and as short as 4 mm. Lateral margins of phylloclade at terminal areole exposed to sun can be very red. Axiallary areoles — Typically there are 4 axial areoles on one side of the phylloclade and five on the other, with the areoles alternating. Typically these areoles have 3 to 4 acicular bristles without glochidia, especially in the upper areoles. Uppermost axiallary areoles also have short hair. Bristles of the axiallary areoles are often shorter than the bristles of areole at the apex of the phylloclade. Blunt teeth are also found with the axiallary areoles.

Buds:

*General.*—Unarmored and ovoid. Color of tepals of buds are generally R.H.S. 46 A (red group). From 1 to 6 flower buds can form on the elongated terminal areole of the uppermost phylloclades. Most of the buds on the uppermost phylloclades will fall of the plant before the flowers bloom; however, when the plant is in full bloom it is common for the uppermost phylloclade to have 2 or more buds of different sizes and age, often with 2 being of similar age and opening simultaneously. Once buds form they grow until maturity or they fall off the plant before flowering. Some buds growing in first axiallary areole. Some buds will also form on the second highest phylloclade of a branch, sometimes as many as three, but more typically 1 or 2.

Flowers:

*General.*—Sessile, actinomorphic, terminal, perfect and epigynous with tepals (undifferentiated whorled sepals and petals) having a spiral emergence as a perianth. Perianth, androecium and gynoecium separate easily from ovary when pulled from the ovary, but if undisturbed will wither attached to the ovary.

*Perianth.*—General: Free, whorled tepals inserted on top of the ovary. Tepals become more reflexed as the flower ages. When the flower is mature there are often 5 very small sepals whose color ranges from R.H.S. 46 A (red group) to R.H.S. 175 B (greyed-orange group). These sepals are approximately 4 mm in length, are lanceloate with entire margins and acute tips, have a glabrous texture, become reflexed as they age. As many as 21 tepals on a flower. Shape: Lanceolate with entire margins and very acute tips. Texture: Glabrous Size: Largest tepals of mature flower is 4 cm. Fully opened flower generally has a diameter of between 5 cm to 5.7 cm. Color: Tepals are thin. Tepals are uniformly dark. Overall color appearance of tepals is R.H.S. 45 A (red group). Upper two-thirds of tepals are R.H.S. 46B (red group) and base is R.H.S. 47D (red group). Older tepals on abaxial side become R.H.S. 51A (red group).

*Androecium* (*stamens*).—General: Numerous stamens (often more than 70) with outermost stamens having filaments basally fused to the perianth. Filaments are basally attached to the anther. Stamens are inserted with respect to the sepals, but become exserted as the tepals become reflexed. Color: Filaments are mostly R.H.S. 74B and are darker than the perianth, but are R.H.S. 155 D (white group) at top. Pollen color: R.H.S. 21A. Pollen diameter averages 71.3 microns with a standard deviation of 4.5 microns. Texture: Filament is glabrous. Size: Stamen filaments s are approximately 10 to 19 mm long, and the anthers are approximately 1 mm long.

*Gynoecium* (*pistil*).—General: Compound ovary with parietal placentation (generally 5 carpels), having a united style, that is of equal length as stamens, and inserted in tepals, but becoming exserted as tepals become reflexed. Style: The base of the style is R.H.S. 155 D (white group) and the top of the style is R.H.S. 74 D (red-purple group) to R.H.S. 44A (red group). The style is typically 23 mm long. Glabrous and without hairs. Stigma: Erect and become reflexed as it ages with usually 5 lobes (but there can be as many as 8 lobes) that are also R.H.S. 155 D on the abaxial side and and R.H.S. 74 D (red-purple group) on the adaxial side. Ovary: General — Compound ovary with a single cavity and parietal placentation and generally 5 carpels, with numerous ovules. The ovary is inferior and obovate to terete with five angles and generally broadening from insertion to floral end. Generally, mature ovaries have a diameter of about 7 mm. Color — R.H.S. 46A (red group ) to R.H.S. 175A,B (greyed-orange group) to R.H.S. 178A (greyed-red group).

*Bloom life.*—New buds may appear and flower on plants that bloomed in January as late as June. Individual flowers last for 10 to 14 days. Plants appear to be in full bloom for approximately 20 days, when they are forced to bloom in January. Over the 20 day period, individual flowers open in the morning and close slightly at night, closing less and less with each day, and the tepals become more reflexed. As the flowers age, the tepals become dessicated but remain attached to the ovary. Tepals and ovary eventually fall off phylloclade together.

*Fruit.*—General: ovaries wither and fall from phylloclades with flower.

*Stomatal density.*—Stomatal density is 13.8 per $mm^2$ plus or minus 4.0.

*Chromosome number.*—Chomosome number is 2n=3x=33.

I claim:

1. The new and distinct hybrid plant of the Cactaceae family substantially as herein shown and described.

* * * * *